(12) United States Patent
Suslov

(10) Patent No.: US 6,443,948 B1
(45) Date of Patent: Sep. 3, 2002

(54) PLASMA KNIFE

(75) Inventor: Nikolaj Suslov, Gothenburg (SE)

(73) Assignee: Nikval International AB, Gothenburg (SE)

( * ) Notice: Subject to any disclaimer, the term of this patent is extended or adjusted under 35 U.S.C. 154(b) by 0 days.

(21) Appl. No.: 09/719,691

(22) PCT Filed: Jun. 10, 1999

(86) PCT No.: PCT/SE99/01013

§ 371 (c)(1),
(2), (4) Date: Feb. 20, 2001

(87) PCT Pub. No.: WO99/66852

PCT Pub. Date: Dec. 29, 1999

(30) Foreign Application Priority Data

Jun. 24, 1998 (SE) .............................................. 9802238

(51) Int. Cl.[7] .............................................. A61B 18/14
(52) U.S. Cl. ..................... 606/40; 606/49; 219/121.36; 219/121.54
(58) Field of Search ................ 606/40, 49; 219/121.36, 219/121.54

(56) References Cited

U.S. PATENT DOCUMENTS

| 4,781,175 A | 11/1988 | McGreevy et al. |
| 4,901,720 A | 2/1990 | Bertrand |
| 5,843,079 A | 12/1998 | Suslov |

FOREIGN PATENT DOCUMENTS

| SE | 503 334 | 5/1996 |

*Primary Examiner*—Lee Cohen
(74) *Attorney, Agent, or Firm*—Pillsbury Winthrop LLP

(57) ABSTRACT

A device for stopping a bleeding in living tissue in humans and animals by forming a necrotic layer in the tissue comprises a member for generating a dynamic plasma flow capable of wholly or partially penetrating an outer, porous layer of the necrotic layer. The device also has an electro-surgical generator arranged to transfer electric energy to the inner limit of the porous layer through a circuit that comprises the plasma flow and the tissue.

8 Claims, 1 Drawing Sheet

PLASMA KNIFE

FIELD OF THE INVENTION

The present invention relates to a device for stopping a bleeding in living tissue in humans and animals by forming a necrotic layer in the tissue, the device comprising a means for generating a dynamic plasma flow of such a character that it is capable of wholly or partially penetrating an outer, porous layer of the necrotic layer.

The invention also relates to a method for use of such a device.

TECHNICAL BACKGROUND

One way of stopping bleedings in connection with surgery is by forming a necrotic layer (death of living tissue) on the bleeding tissue. Today a plurality of methods are available to form such a layer, inter alia, treatments with a plasma jet, laser irradiation, or electrosurgery. A common feature of all these methods is that a bleeding tissue is supplied with energy, forming a necrotic layer on the surface of the wound, which stops the bleeding. The necrotic layer usually consists of several layers. On the outside a porous necrotic layer forms, where the fluid component of the tissue has been vaporised by the supplied energy. The inner boundary of the porous layer thus constitutes the fluid limit of the tissue. Underneath this layer proteins in the tissue are denatured because of a rise in temperature, whereby a compact necrotic layer forms. The two layers together form the necrotic layer which stops the bleeding.

In order to stop the bleeding efficiently the necrotic layer has to be formed at a higher speed than the flow rate of the blood out of the tissue. At the same time the effect adjacent to the surface of the tissue must not be too great since the outer, porous layer is sublimed at temperatures that are too high. The problem is made worse by the low heat conductivity of the porous layer.

A device which utilises a plasma jet to form the necrotic layer is known from SE 503 334. The device which is described in this publication has the advantage of providing a dynamic plasma flow, the character of which is such that it is capable of penetrating an upper porous necrotic layer, such that when the plasma jet is directed towards a tissue, a great part of the flow energy is conducted to the fluid limit of the tissue.

The above device operates well to stop small to middle-sized bleedings. Bleedings from blood-vessels with a diameter of 3 and 4 mm for arteries and veins, respectively, can be successfully stopped. However, in connection with very heavy bleedings, such as from thick blood vessels within, for instance, the liver, the blood stopping capacity is insufficient.

Another known technique for stopping bleedings by forming a necrotic layer on the tissue is the electrosurgical technique, which is shown in, for instance, U.S. Pat. No. 4,781,175. Here electric high-frequency energy is conducted from an electrosurgical generator through a circuit comprising a gas jet, which is directed towards the tissue, the patient, and a diathermic plate connected to the patient. The electric energy is conducted to the tissue by the gas jet in the form of a diffuse current. This causes necrosis on the surface of the tissue. The formed necrotic layer is compact and relatively thin, and therefore, this technique can only be used in connection with small, capillary bleedings.

In order to stop a more extensive bleeding a larger amount of electric energy is required. As the amount of energy from the generator thus increases, electric arcs and sparks between the surgical instrument and the tissue appear. During the use of large amounts of energy a necrotic layer is formed, which consists of both a compact and a porous layer. Because of the influence of the sparks and the electric arcs, the porous layer is, however, formed with depressions and is more porous, and thus also brittler than desired. Moreover, in the formation of electric sparks there is a rectification of the alternating current, a rectified current passing through the patient. This current causes an unintentional excitation of nerves and muscles. This excitation can be injurious in connection with, for instance, heart diseases. Another disadvantage is that relatively high voltages (2000 V) are required to obtain a satisfying effect.

The use of the method is limited to middle-sized bleedings owing to, inter alia, the previously mentioned problem caused by the insufficient heat conductivity and sublimation of the porous layer. Neither does the necrotic layer form so quickly that a bleeding from, for instance, a thick blood-vessel can be stopped.

SUMMARY OF THE INVENTION

The object of the present invention is to provide a device, which allows a better and quicker stopping of a bleeding. In particular, it should be possible to stop heavy bleedings from relatively thick blood-vessels. At the same time the patient should not risk being exposed to potentially injurious, rectified currents.

According to the invention, this object is achieved by means of a device which comprises a means for generating a dynamic plasma flow of such a character that it is capable of wholly or partially penetrating an outer, porous layer of the necrotic layer. The device is characterized in that an electrosurgical generator is arranged to transfer electric energy to the fluid limit of the tissue through a circuit, which comprises the plasma flow and the tissue.

The above device is used according to the inventive method, which comprises the steps of generating the plasma flow and directing it towards a bleeding tissue, whereby a necrotic layer comprising a porous and a compact layer forms in the bleeding tissue. Electric high-frequency energy is transferred to the tissue through an electric circuit which comprises the plasma jet and the tissue, the electric energy being conducted through the plasma jet to the fluid limit of the tissue for increasing the thickness of the compact necrotic layer.

The dynamic, hot plasma flow quickly forms a necrotic layer on the tissue. The formed outer, porous necrotic layer has no depressions. Furthermore, the plasma flow is a nearly ideal conductor for the electric energy, which owing to the penetrating effect of the plasma is conducted directly to the fluid limit of the tissue, where it quickly causes an increase of the compact layer in the necrotic layer. The voltage in the electrosurgical generator can be low (<200 V), and neither sparks nor electric arcs appear. Thus there will be no difficulties in rectifying the alternating current from the generator.

Preferably, one of the poles of the electrosurgical generator is connected to an electrode in the plasmagenerating means and its other pole to a diathermic plate to be connected to the patient.

Advantageously, an electric switch is arranged for manually switching on and off the electrosurgical generator. It is then possible to use a method where electric high-frequency energy is supplied instantaneously to stop especially heavy bleedings in the tissue, for instance, in thick blood-vessels.

In this case the electrosurgical function is used only when necessary. The plasma function is sufficient on most of the wound surfaces. Thus, the device and the method will be flexible and easy to use in connection with different types of surgery.

Preferably, the outer casing of the plasmagenerating means is an electrically non-conductive body. Otherwise, further insulation is required to prevent the casing from being conductive when the electrosurgical generator is switched on.

DESCRIPTION OF PREFERRED EMBODIMENTS

Figure 1:
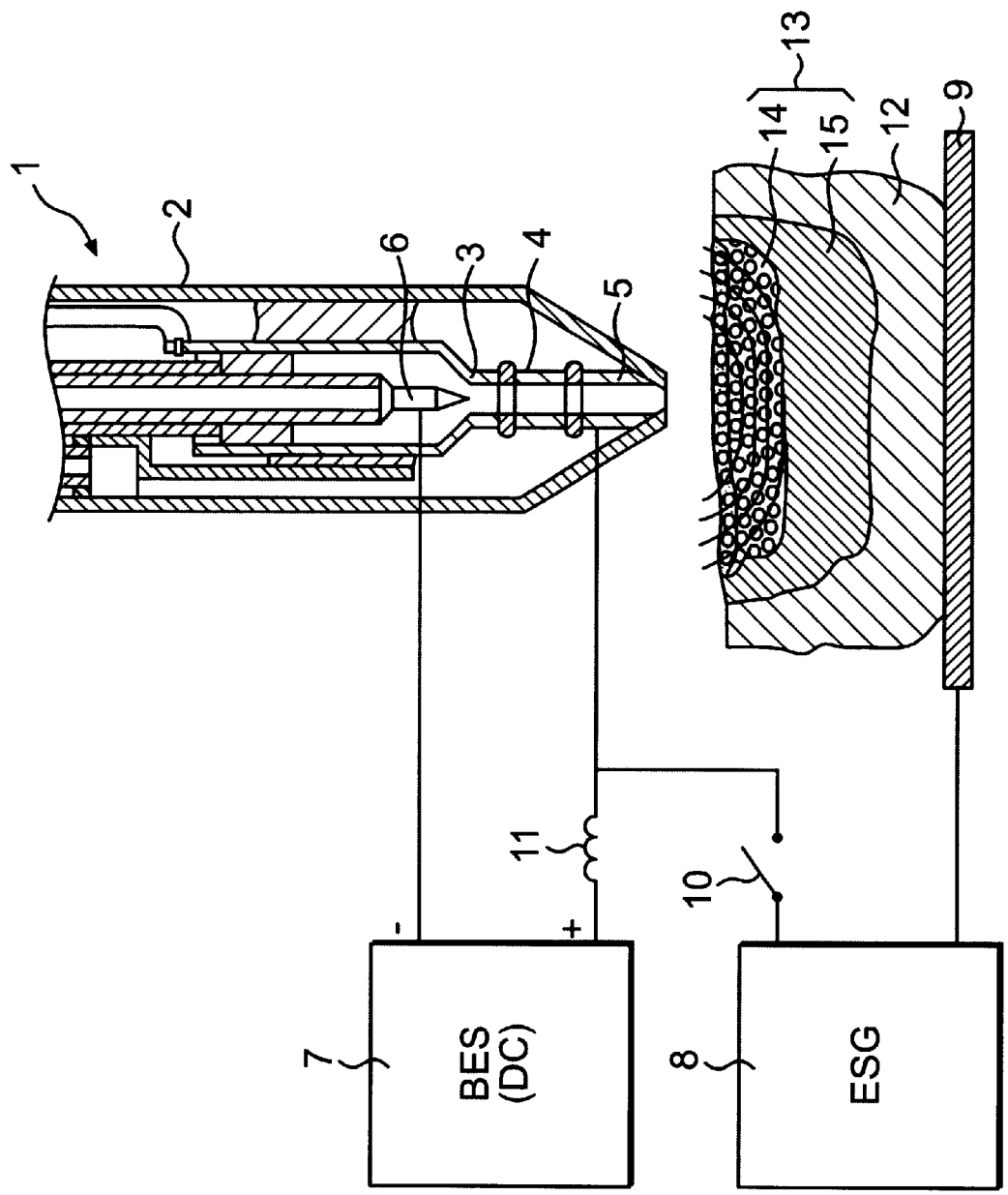
FIG. 1 is a schematic view of a preferred embodiment of the device according to the invention.

FIG. 1 shows a plasma-generating means 1 consisting of an electrically non-conductive body 2, which has the form of a pen. The body 2 has a cylindrical duct intended for heating a plasma-generating gas. The duct is formed of sections 3, 4, 5, which are electrically insulated from each other. At the inner end of the duct there is a cathode 6, which is connected to the negative pole of a basic energy source 7 (BES). The outer section 5 of the duct is connected to the positive pole of the basic energy source 7.

The means for transferring electric energy consists of an electrosurgical generator 8 (ESG), one pole of which is connected to the outer section 5 of the duct, and the other pole of which is connected to a diathermic plate 9, which is placed in contact with the patient. The circuit in which the electrosurgical generator is included is provided with an electric switch 16 for switching on and off the electrosurgical function. The electric switch can be operated by the surgeon. This may take place by means of, for instance, a button in connection with the body 2, or pedals. FIG. 1 also shows a coil 11, which is placed between the positive pole of the energy source 7 and the electrosurgical generator 8. The coil 11 prevents a possible influence on the basic energy source 7 from the generator 8.

Over the greater part of the surface of the wound only the plasma function is used, since this is sufficient to stop small to middle-sized bleedings. In the tissue 12, a necrotic layer 13 forms consisting of an outer, porous layer 14 and an inner, compact layer 15. Where the bleeding is particularly severe, for instance, where there is a thick blood-vessel, the surgeon temporarily switches on the generator 8 by means of the electric switch 10. Then an alternating current is generated, which is conducted to the tissue 12 through the plasma. Owing to the plasma penetrating the porous necrotic layer 14, the electric energy is directly conducted down to the fluid limit of the tissue, where it forms a thicker necrotic layer, which is sufficient to stop even this heavy bleeding. Because of the high conductivity of the plasma neither sparks nor electric arcs appear, thus avoiding the disadvantages connected therewith.

In an alternative embodiment, one pole of the electrosurgical generator 8 may instead be connected to the cathode 6 of the plasma-generating means 1. Here, too, the other pole is connected to the diathermic plate 9. However, in this embodiment the path of the alternating current through the plasma becomes longer than in the first embodiment, which results in a somewhat greater loss of energy.

It will be appreciated that further embodiments are possible within the scope of the invention. Naturally, the circuit diagram for the connection of the electrosurgical generator may be designed in many ways in order to conduct the current through the plasma jet.

What is claimed is:

1. A device for stopping a bleeding in living tissue in humans and animals by forming a necrotic layer in the tissue, the device comprising:

a means for generating a dynamic plasma flow, the plasma flow forms a necrotic layer comprising a porous layer and a compact layer when directed at the tissue, and the plasma flow being capable of wholly or partially penetrating an outer, porous layer of the necrotic layer; and an electrosurgical generator arranged to transfer electric energy to an inner limit of the porous layer in the necrotic layer through a circuit, the circuit comprises the plasma flow and the tissue.

2. A device according to claim 1, wherein the means for generating a dynamic plasma flow comprises a basic energy source and the electrosurgical generator comprises a first pole and a second pole and a diathermic plate, said first pole being connected to the basic energy source for the plasma-generating means, and the second pole being connected to the diathermic plate for connection to the patient.

3. A device according to claim 1 or 2, wherein the plasma generating means comprises an outer section connected to one pole of the electrosurgical generator.

4. A device according to claim 1 or 2, wherein the plasma generating means comprises a cathode connected to one pole of the electrosurgical generator.

5. A device according to claim 1, further comprising an electric switch arranged for manually switching on and off the electrosurgical generator.

6. A device according to claim 1, wherein the plasma-generating means has an outer casing consisting of an electrically non-conductive material.

7. A method for stopping a bleeding in a living tissue in humans and animals by forming a necrotic layer in the tissue, comprising:

generating a dynamic plasma flow capable of wholly or partially penetrating an outer, porous layer of the necrotic layer;

directing said dynamic plasma flow in the form of a plasma jet towards a bleeding tissue so that the necrotic layer comprising a porous and a compact layer forms in the tissue, the plasma flow capable of wholly or partially penetrating an outer, porous layer of the necrotic layer;

transferring electric energy to the tissue through a circuit which comprises the plasma jet and the tissue, and conducting the electric energy through the plasma jet to an inner limit of the porous necrotic layer for increasing the thickness of the compact layer.

8. A method according to claim 7, further comprising supplying intantaneously electric energy to stop especially heavy bleedings in the tissue.

* * * * *